United States Patent
Hallen (10) Patent No.: US 11,166,843 B2
(45) Date of Patent: Nov. 9, 2021

(54) ENTRY CANNULA WITH INTRAOCULAR PRESSURE ACTIVATED SEAL

(71) Applicant: NOVARTIS AG, Basel (CH)

(72) Inventor: Paul R. Hallen, Colleyville, TX (US)

(73) Assignee: Alcon Inc., Fribourg (CH)

( * ) Notice: Subject to any disclaimer, the term of this patent is extended or adjusted under 35 U.S.C. 154(b) by 166 days.

(21) Appl. No.: 15/994,058

(22) Filed: May 31, 2018

(65) Prior Publication Data

US 2018/0353326 A1 Dec. 13, 2018

Related U.S. Application Data

(60) Provisional application No. 62/518,811, filed on Jun. 13, 2017.

(51) Int. Cl.
*A61F 9/007* (2006.01)
*A61B 17/34* (2006.01)
(Continued)

(52) U.S. Cl.
CPC .......... *A61F 9/007* (2013.01); *A61B 17/3462* (2013.01); *A61B 17/3498* (2013.01);
(Continued)

(58) Field of Classification Search
CPC .. A61F 9/007; A61F 9/00736; A61B 17/3462; A61B 17/3498;
(Continued)

(56) References Cited

U.S. PATENT DOCUMENTS 3,528,410 A 9/1970 Banko
3,659,607 A 5/1972 Banko
(Continued)

FOREIGN PATENT DOCUMENTS

EP 2002812 A1 12/2008
EP 2002812 A1 12/2008
(Continued)

OTHER PUBLICATIONS

Edge Plus Blade Valved Entry System. Novartis 2011. GAU11166SA.
(Continued)

*Primary Examiner* — Nathan R Price
*Assistant Examiner* — John A Doubrava (57) ABSTRACT

A valved trocar cannula for insertion into an eye includes a trocar cannula having a distal end configured to be positioned within the eye and a proximal end configured to be positioned outside the eye. An elastomeric membrane or seal is attached to the trocar cannula at the proximal end thereof and restricts a free flow of fluid from within the trocar cannula to outside the proximal end of the trocar cannula. The elastomeric membrane includes at least one slit extending therethrough and is arranged to permit the passage of a surgical instrument through the membrane and into the trocar cannula. The slit may through the elastomeric membrane at an oblique angle along a least a portion of the slit. Pressure applied across a first surface or a second surface of the elastomeric membrane in a vicinity of the slit tends to keep the slit in a closed position.

11 Claims, 8 Drawing Sheets

(51) Int. Cl.
*A61M 39/06* (2006.01)
*A61B 17/00* (2006.01)

(52) U.S. Cl.
CPC ......... *A61F 9/00736* (2013.01); *A61M 39/06* (2013.01); *A61B 2017/00862* (2013.01); *A61M 2039/064* (2013.01)

(58) Field of Classification Search
CPC ..... A61B 2017/00862; A61B 17/3415; A61M 39/06; A61M 2039/2426; A61M 2039/064
See application file for complete search history.

(56) References Cited

U.S. PATENT DOCUMENTS

| | | | |
|---|---|---|---|
| 4,798,594 A * | 1/1989 | Hillstead | A61M 39/0606 137/849 |
| 5,779,697 A | 7/1998 | Glowa | |
| 7,637,893 B2 * | 12/2009 | Christensen | A61B 17/3415 604/167.04 |
| 8,062,260 B2 | 11/2011 | McCawley | |
| 8,277,418 B2 | 10/2012 | Martin et al. | |
| 8,343,106 B2 | 1/2013 | Lopez | |
| 8,771,223 B2 | 7/2014 | Patton et al. | |
| 2005/0049555 A1 * | 3/2005 | Moorehead | A61M 25/0045 604/122 |
| 2005/0096695 A1 | 5/2005 | Olich | |
| 2011/0087093 A1 * | 4/2011 | Buiser | A61M 39/24 600/435 |
| 2011/0152775 A1 * | 6/2011 | Lopez | A61F 9/007 604/167.01 |

FOREIGN PATENT DOCUMENTS

| | | |
|---|---|---|
| WO | 9602297 A1 | 2/1996 |
| WO | WO9602297 A1 | 2/1996 |
| WO | 2008045744 A2 | 4/2008 |
| WO | WO2008045744 A2 | 4/2008 |

OTHER PUBLICATIONS

Eckardt, Claus, "Transconjunctival Sutureless 23-Gauge Citrectomy," Retina, the Journal of Retinal and Vitreous Diseases, vol. 25, Nov. 2, 2005.

Edge Plus Blade Valved Entry Sysem; Novartis 2011 GAU11166SA.

* cited by examiner

ENTRY CANNULA WITH INTRAOCULAR PRESSURE ACTIVATED SEAL

TECHNICAL FIELD

The present disclosure generally pertains to ophthalmic surgery. More particularly, but not by way of limitation, the present disclosure pertains to ophthalmic trocar cannulas.

BACKGROUND

Microsurgical instruments may be used by surgeons for removal of tissue from delicate and restricted spaces in the human body, e.g., in surgery on the eye. In the context of ophthalmic surgical procedures, microsurgical instruments may be used to remove the vitreous body, blood, scar tissue, or the crystalline lens, or to repair retina detachments and treat retina diseases. Such instruments may be in the form of a surgical handpiece that a user, such as a surgeon or other medical professional, uses to dissect and remove tissues, such as any of those described above. The surgical handpiece may be coupled to a control console.

With respect to posterior segment surgery, the handpiece may be a vitreous cutter probe, a laser probe, or an ultrasonic fragmenter for cutting or fragmenting the tissue and may be connected to the control console by a pneumatic line and/or power cable, optical cable, or flexible tubes for supplying an infusion fluid to the surgical site and for withdrawing or aspirating fluid and cut/fragmented tissue from the site. The cutting, infusion, and aspiration functions of the handpiece may be controlled by the control console that not only provides power for the surgical handpiece(s) (e.g., power to operate a reciprocating or rotating cutting blade or an ultrasonically vibrated needle), but may also control the flow of infusion fluid and provide a source of vacuum (relative to atmosphere) for the aspiration of fluid and cut/fragmented tissue. The functions of the console may be controlled manually by the surgeon (e.g., through use of a foot-operated switch or proportional control).

During posterior segment surgery, the surgeon may use several handpieces or instruments during the procedure. This procedure may require that these instruments be inserted into, and removed out of the incision. This repeated removal and insertion may cause trauma to the eye at the incision site. To address this concern, hubbed cannulae may be used to introduce instruments into the eye. Hubbed cannulae may include a narrow tube with an attached hub. The tube may be inserted into an incision in the eye up to the hub, which may act as a stop, limiting the amount by which the hubbed cannulae may be inserted into the incision. The hub may be stitched to the eye to prevent inadvertent removal. Surgical instruments can be inserted into the eye through the tube, and the tube may protect the incision sidewall from repeated contact by the instruments. In addition, the surgeon may use the handpiece, by manipulating the handpiece when inserted into the eye through the tube of the hubbed cannulae, to help position the eye during surgery.

SUMMARY

Slits in prior closed cannula systems are generally perpendicular to the elastomeric material's face. These slits have a tendency to open up, as intraocular pressure increases. This can allow more leakage, and may permit streams of fluid to be ejected from the eye, through the cannula, during surgical procedures, especially when instruments are removed from the eye.

In several embodiments of the present disclosure, the slit geometry is designed so as to take advantage of intraocular pressure, to create apposition of one elastomeric edge against the other, like a flap. This approach creates an overlapping valve seat that provides increasing protection leakage at higher pressures.

One aspect of the present is directed to a valved trocar cannula that includes a cannula and an elastomeric membrane. The cannula may be sized and shaped to be inserted into an eye and may include a distal end configured to be positioned within the eye when in use and a proximal end configured to be positioned outside the eye when in use. The elastomeric membrane may include a first surface at a proximal end of the elastomeric membrane, a second surface at a distal end of the elastomeric membrane, a thickness extending from the first surface to the second surface, and at least one slit extending through the elastomeric membrane and at least a portion of the slit forming an oblique angle relative to the first surface and second surface of the elastomeric membrane. The slit may have a length extending along the first surface and the second surface of the elastomeric membrane and may be arranged to permit the passage of a surgical instrument through the elastomeric membrane and into the cannula. The elastomeric membrane disposed at the proximal end of the cannula and connected to the cannula and restricting a free flow of fluid from within the cannula to outside the proximal end of the cannula.

The aspects of the disclosure may include one or more of the following features. The oblique angle formed by the slit may extend through the elastomeric membrane along an entirety or a majority of the length of the slit. The oblique angle may be less than approximately 75 degrees. The oblique angle may be approximately 45 degrees. A cross-sectional shape of the slit may change direction continuously or at one or more points. An overcap may be coupled to the proximal end of the cannula, and the elastomeric membrane may be attached to the proximal end of the overcap. The overcap may include a plurality of apertures formed in the proximal end thereof, and the elastomeric membrane may be received into the plurality of apertures. The overcap may include at least one slot formed in a side of the overcap, and the cannula may include at least one tab. The at least one tab may be received into the at least one slot to form an interlocking connection between the overcap and the cannula. The interlocking connection between the overcap and the cannula may prevent rotation of the overcap relative to the cannula. The overcap may define a flange defining an opening, and the elastomeric membrane may sandwich the flange between a first end and a second end of the elastomeric membrane.

The above systems and/or apparatuses may be used with the above methods and vice versa. In addition, any system or apparatus described herein may be used with any method described herein and vice versa. It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE FIGURES

For a more complete understanding of the present disclosure, reference is made to the following description taken in conjunction with the accompanying drawings in which:

FIGS. 4b and 4c are cross-sectional views of the overcap and seal of FIG. 4a;

It is to be understood that both the foregoing general description and the following detailed description are exemplary and explanatory only and are intended to provide a further explanation of the present disclosure as claimed.

DETAILED DESCRIPTION

Following is a detailed description of an example closed trocar cannula, based on designs illustrated and described in U.S. Pat. No. 8,277,418 B2, the entire contents of which are incorporated herein by reference, to provide additional details and context for the devices and techniques described herein. It will be appreciated, however, that the improvements described herein, and in particular the improved slit designs described below, may be applied to closed cannulae having features that differ from those illustrated and explained herein, in ways that may not be directly relevant to the improvements described herein.

Figure 1:
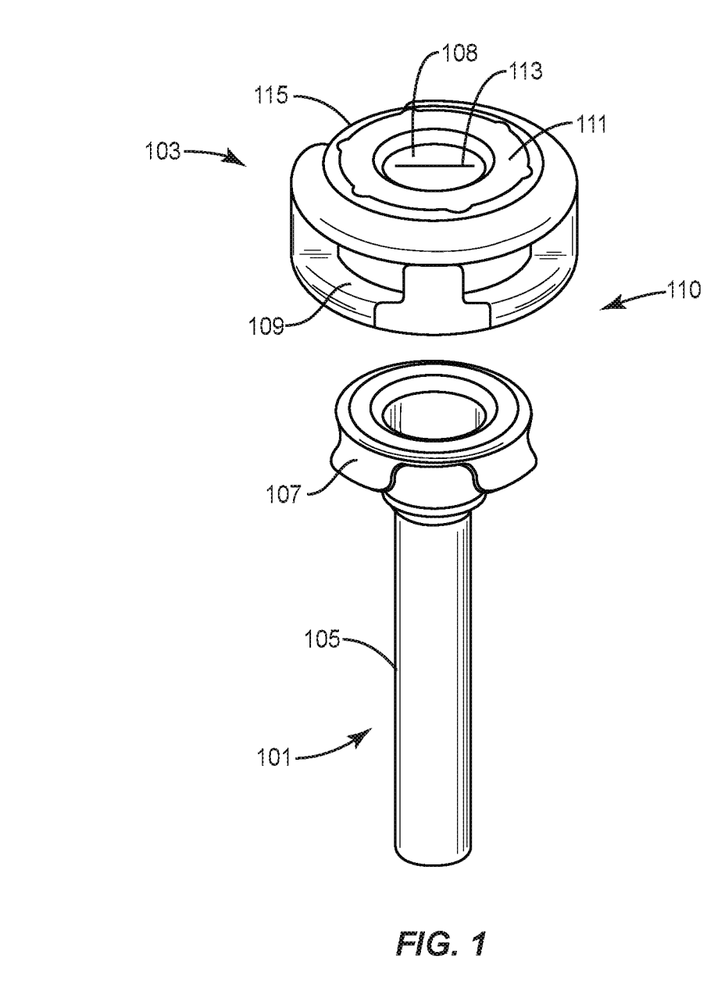
FIG. 1 illustrates an example trocar cannula and overcap.

FIG. 1 illustrates an example embodiment of a trocar cannula 101 and an overcap 103. The trocar cannula 101 may be configured for insertion into an eye to facilitate insertion and removal of instruments during surgery. The cannula 101 includes a shaft 105 capable of extending into the eye (e.g., through a sclera, conjunctiva, etc.) so that a distal end of the trocar cannula 101 is positioned within the eye during use. In some embodiments, the trocar cannula 101 may be attached to the overcap 103, at a proximal end of the trocar cannula 101. For example, the trocar cannula 101 may include one or more tabs 107 receivable corresponding slots 109 on the trocar cannula 101. The trocar cannula 101 illustrated in FIG. 1 includes four tabs 107 to engage four corresponding slots 109 on the overcap 103. Additional or fewer tabs 107 and corresponding slots 109 are also contemplated. Other attachment configurations are also contemplated. For example, the trocar cannula 101 may include slots, which may be similar to slots 109, and the overcap may include tabs, which may be similar to tabs 107. In some embodiments, the trocar cannula 101 may be attached to the overcap 103 in other ways. For example, in some instances, the trocar cannula 101 may be coupled to the overcap 103 with an adhesive, via thermal bonding, etc.

In some embodiments, a seal 111 may be coupled to the overcap 103. In some instances, the seal 111 may be over-molded onto the overcap 103 to form a valve. For example, the seal 111 may be disposed at least partially between the shaft 105 and the overcap 109, as shown, for example, in FIG. 8. Referring again to FIG. 1, a surface 108 of the seal 111 may be exposed on the overcap 109. A slit 113 is formed in the seal 111 to allow passage of surgical tools into the cannula 101. When an instrument or other device is inserted through the seal 111, the slit 113 opens, permitting passage of the instrument or other device through the seal 111. In some implementations, more than one slit may be formed in the seal 111. Where no instrument is inserted through the slit 113, the slit 113 remains in a closed configuration, inhibiting fluid flow through the seal 111.

Figure 2:
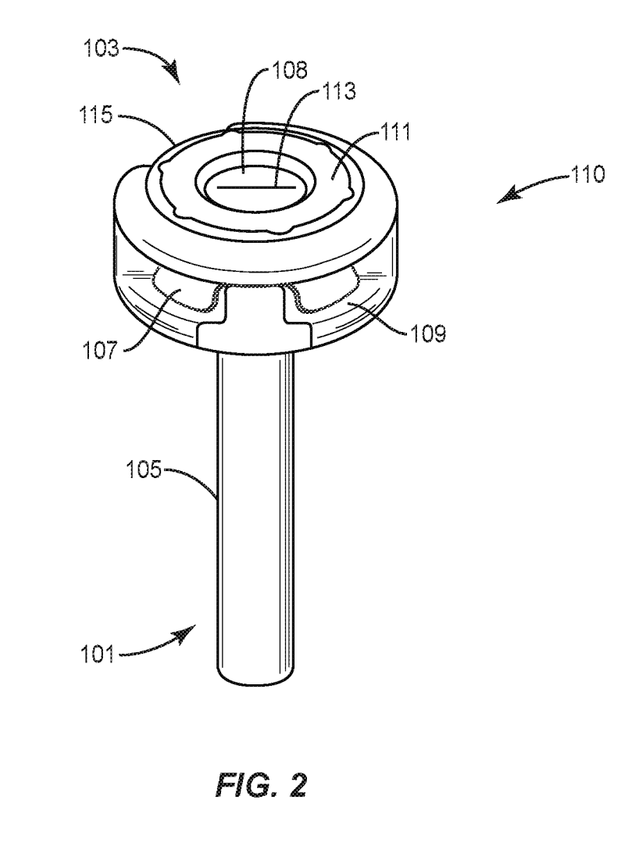
FIG. 2 shows the trocar cannula and the overcap of FIG. 1 affixed to each other to form a valved trocar cannula.

FIG. 2 illustrates the cannula 101 affixed to the overcap 103, e.g., after engagement of the tabs 107 in respective slots 109. As combined, the cannula 101, the overcap 103 and the seal 111 form a valved trocar cannula 110. In some embodiments, the tab/slot interface may prevent rotation of the overcap 103 relative to the cannula 101, e.g., during insertion of the distal end of cannula 101 into the eye. In some embodiments, the tabs 107 may be configured to permanently hold the overcap 103 to the cannula 101, i.e., such that the overcap 103 may not be removed from the cannula 101 without destroying part of the cannula 101 and/or overcap 103. For example, the tabs 107 (and cannula 101) may be made of stainless steel and the overcap 103 may be made of plastic, e.g., polycarbonate. Other materials are also contemplated. For example the cannula 101 may be formed from other metals, such as titanium, plastics, or other applicable materials. In some instances, the overcap 103 may be formed from metals, e.g., stainless steel or titanium, or other applicable materials. The permanent hold between the overcap 103 and the cannula 101 may prevent inadvertent removal of the overcap 103 from the cannula 101 during surgery (e.g., vitreoretinal surgery).

Figure 3A:
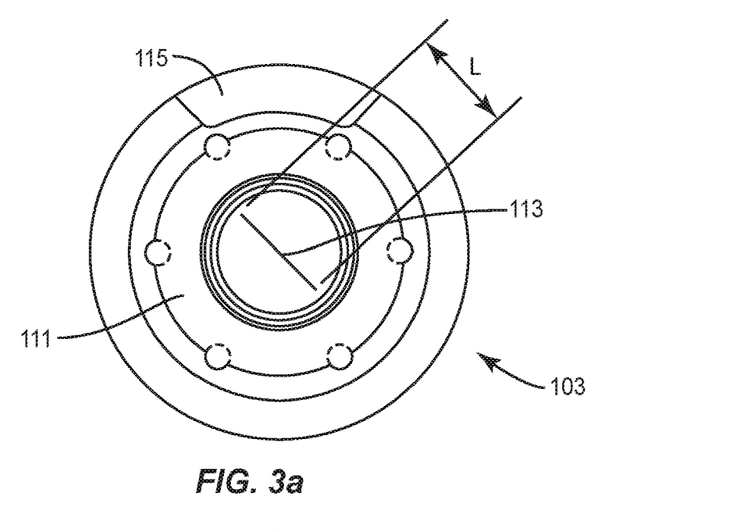
FIG. 3a illustrates a top view of the valved trocar cannula of FIG. 2 showing a slit in the seal on the overcap.
Figure 3B:
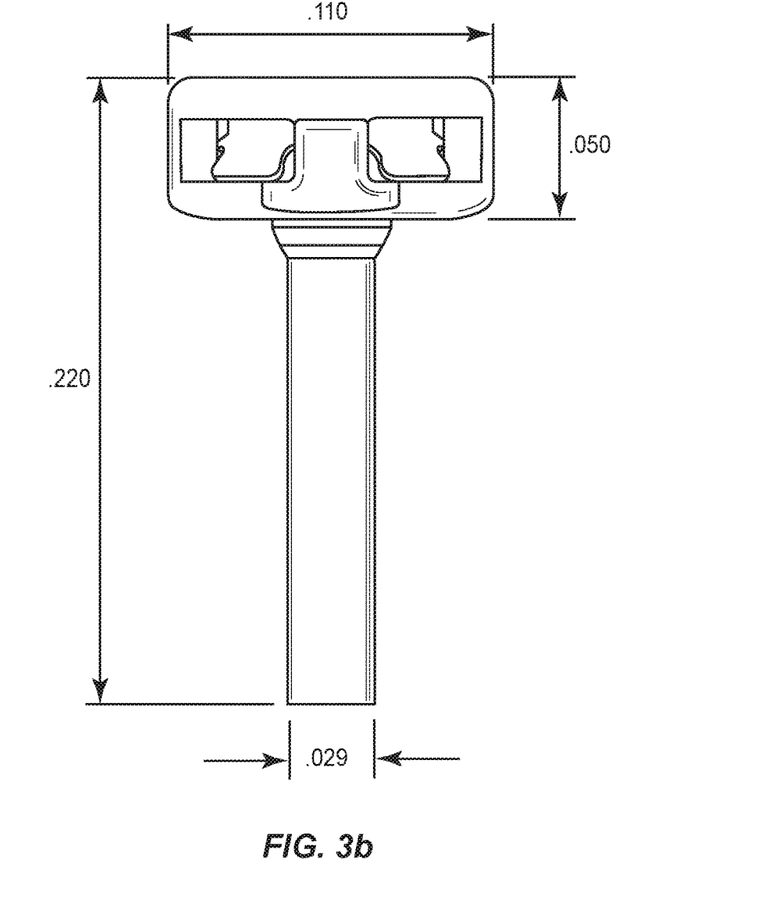
FIG. 3b illustrates a side view of the valved cannula and overcap of FIG. 2 with several example dimensions.

FIG. 3a illustrates a top view of the attached cannula 101 and overcap 103 and shows the slit 113 in the seal 111 on the overcap 103. The slit 113 has a length L extending across the seal 111, as shown. FIG. 3b illustrates a side view of attached the cannula 101 and overcap 103 with several example dimensions (provided in inches). Other dimensions are also contemplated. Thus, the illustrated dimensions are examples only and are not intended to limit the scope of the disclosure. For example, a height of the overcap 103 may be greater or less than 0.050 inches, and an outer diameter of the overcap 103 may be greater or less than 0.110 inches. Similarly, the overall length of the combined cannula 101 and overcap 103 may be less than or greater than 0.220 inches. Further, while an outer diameter of the cannula 101 is shown as 0.029 inches (corresponding to a 23-gauge cannula), in other instances, the outer diameter of the cannula may be 0.0243 inches (for a 25-gauge cannula). Other outer diameters are also contemplated. For example, the outer diameter of cannula 101 may be less than 0.029 inches, between 0.029 inches and 0.0243 inches, or greater than 0.0243 inches.

Figure 4A:
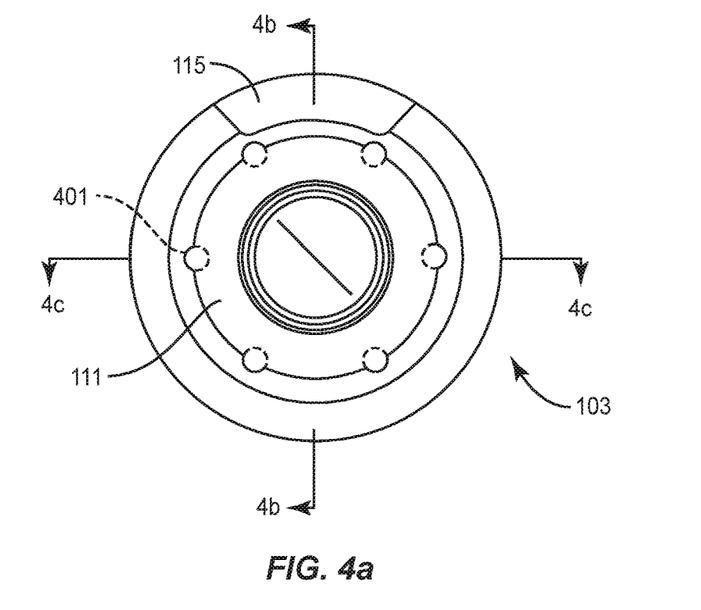
FIG. 4a is a top view of an example overcap.
Figure 4B:
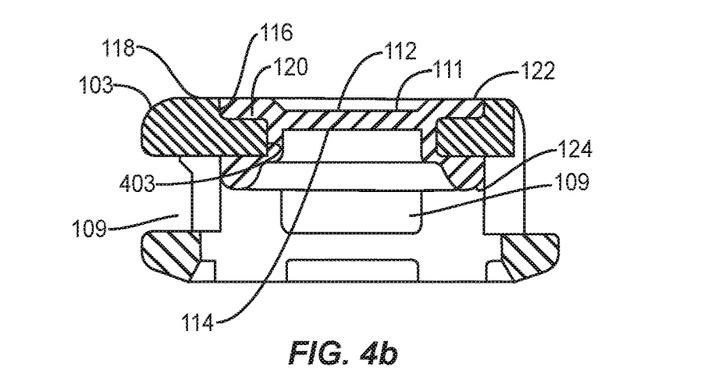
Figure 4C:
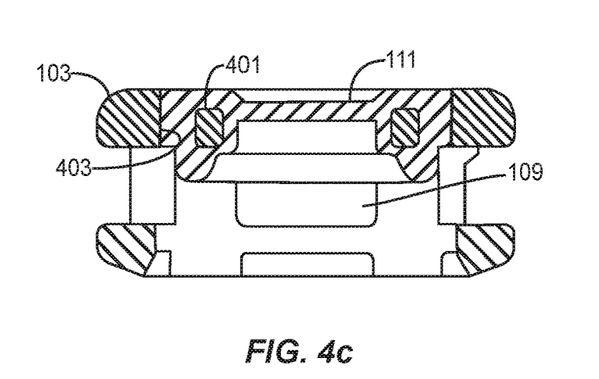
Figure 4D:
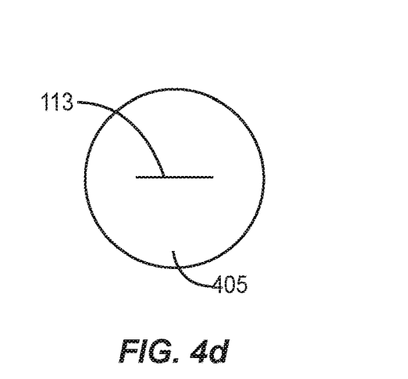
FIG. 4d is a detail view of a silicon wafer that may be included in some implementations of the seal.

FIG. 4a is a top view of the overcap 103 and seal 111. FIGS. 4b and 4c are cross-sectional views taken along the associated lines illustrated in FIG. 4a. The seal 111 may be made of an elastomer (e.g., silicone). When the overcap 103 is affixed to the cannula 101, the seal 111 extends across an opening formed in a distal end of the overcap 103. In some embodiments, the seal 111 may be attached to the overcap 103 to inhibit rotation of the seal 111 relative to the overcap 103. For example, the seal 111 may be overmolded into an opening 403 and one or more apertures 401 formed in the overcap 103. In some embodiments, the seal 111 may include a silicon wafer 405 that is formed separately from the overcap 103 and inserted between the overcap 103 and the cannula 101 during assembly of the overcap 103 onto the cannula 101. In such a case, the seal 111 may be attached to the overcap 103 and cannula 101 through a friction fit. Other attachments are also contemplated. For example, in some instances, the seal 111 having a silicon wafer 405 may be attached with an adhesive.

With reference to FIGS. 4a, 4b, and 4c, the slit 113 extends through the elastomeric membrane of the seal 111 in a direction that is substantially perpendicular to a proximal surface 112 and a distal surface 114 of the elastomeric membrane when the seal 111 is in the closed configuration (i.e., when no instrument is inserted through the slit 113). Below, improved designs of this slit 113 are described in detail.

Referring to FIG. 4b, the overcap 103 forms a recessed opening 116 at a proximal end 118. A flange 120 defining the opening 403 is formed adjacent to the recessed opening 116. The seal 111 may be overmolded onto the overcap 103 or inserted into the overcap 103 so as to sandwich the flange 120 between a first end 122 and a second end 124 of the seal 111.

Figure 5:
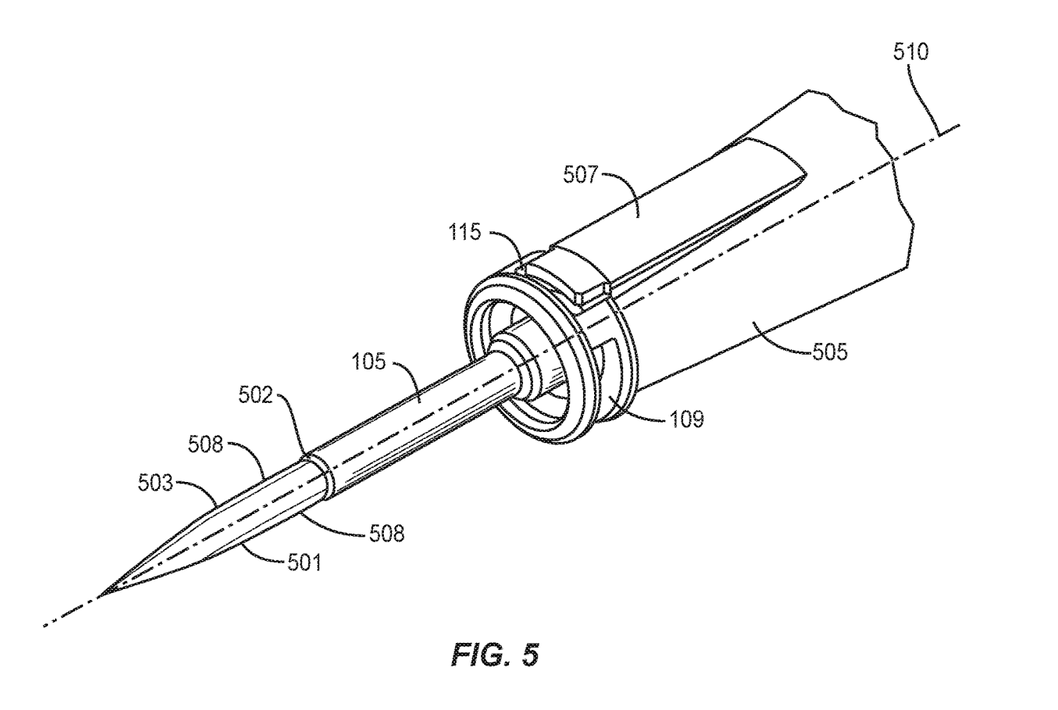
FIG. 5 illustrates an example valved trocar cannula disposed on a trocar inserter.
Figure 12:
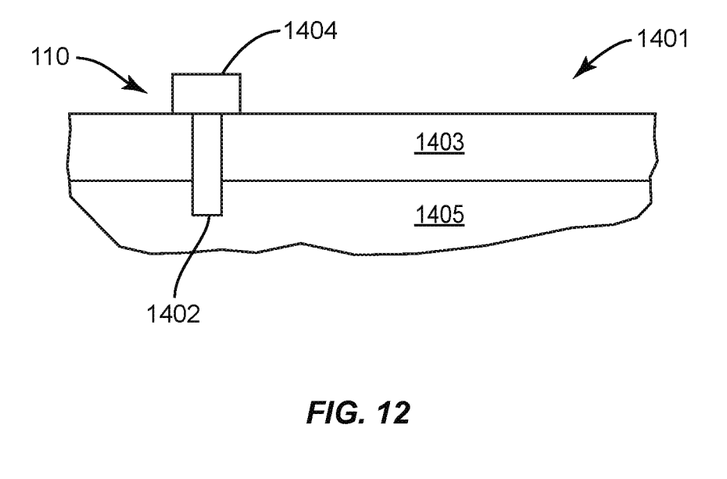
FIG. 12 illustrates a valved trocar cannula inserted into an eye.

FIG. 5 illustrates an embodiment of the cannula 101 on a trocar inserter 501. In some embodiments, the trocar inserter 501 may include a trocar blade 503 attached to a handle 505. In some embodiments, the handle 505 may be made of plastic, and the blade 503 may be made of stainless steel. Other materials are also contemplated. The trocar blade 503 may extend past a distal end 502 of the shaft 105 and may include one or more sharp edges 508 to pierce an eye, e.g., eye 1401 shown in FIG. 12, for insertion of the cannula 101. With reference to FIG. 12, the trocar blade 503 may pierce the sclera 1403 and the vitreous body 1405. Referring again to FIG. 5, in some embodiments, a guide 507 may fit into the guide slot 115 to inhibit rotation of the overcap 103 and/or cannula 101 relative to the handle 505 during insertion of the cannula 101 into the eye. In some embodiments, the guide 507 may releasably engage the guide slot 115 such that when the trocar inserter 501 is withdrawn from the overcap 103 and cannula 101 assembly, the guide 507 does not pull the overcap 103 and cannula 101 assembly out of the eye 1401. For example, the guide 507 may frictionally engage the guide slot 115 with a friction force that is less than a friction force exerted by the eye on the external sides of the cannula 101 when the cannula 101 is into the eye.

While the guide 507 is depicted as a tab to be received into guide slot 115, other interlocking features are also contemplated. For example, the guide 507 and guide slot 115 may include different interlocking features (such as a ring and a rod) or may include other interlocking components, such as interlocking magnets (one on each of the handle 505 and overcap 103), engaging o-rings (one on each of the handle 505 and overcap 103), etc. In some embodiments, engagement between the guide 507 and the guide slot 115 may prevent rotation between the cannula 101 and the overcap 103 so that any rotational movement of the trocar handle 505 about the handle's longitudinal axis 510 may be transmitted to the overcap 103 and then to the cannula 101. Thus, the engagement between the guide 507 and the guide slot 115 may provide vitreoretinal surgeons rotational control of the cannula 101 relative to the trocar handle 505 during insertion of the cannula 101 into the sclera.

Figure 6A:
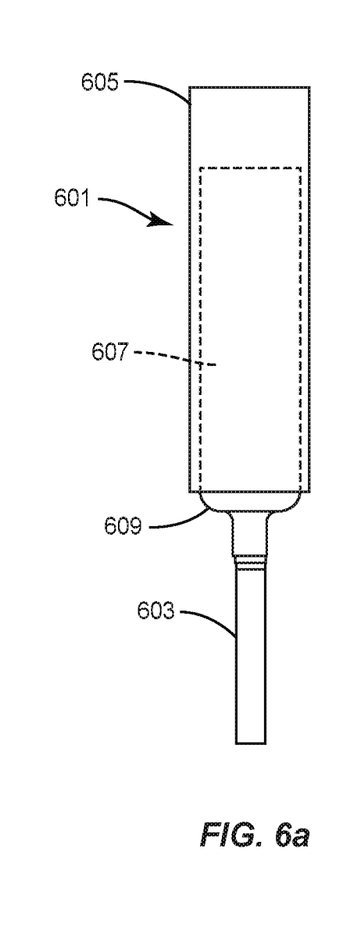
FIGS. 6a and 6b illustrate an example vent.
Figure 6B:
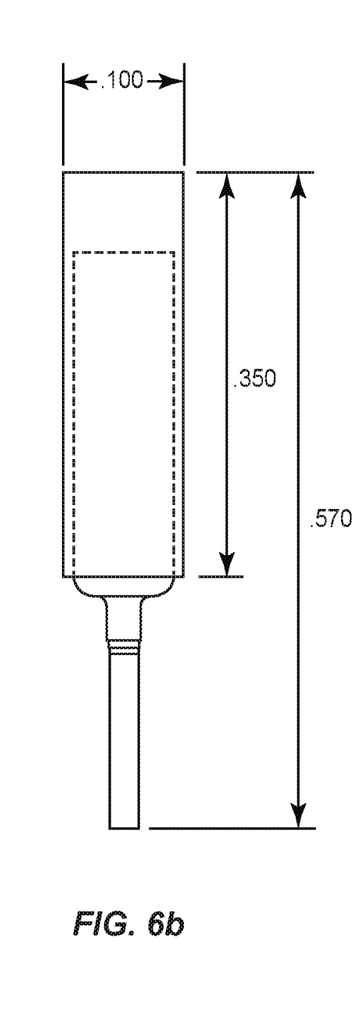
Figure 7:
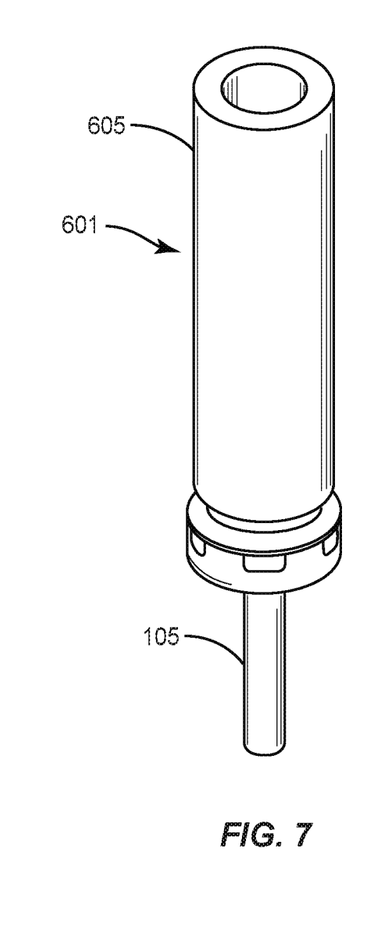
FIG. 7 shows an example vent inserted into a valved trocar cannula.

FIGS. 6a and 6b illustrate an embodiment of a vent 601. While the seal 111 of the valved trocar cannula 110 may close off the cannula from fluid flow into or out of the cannula when, for example, a surgical instrument is occluding the cannula or when no instrument has been introduced through the seal 111 (i.e., when the slit 113 is in the closed configuration), a vent cannula 603 may be configured to slide into the slit 113 of the seal 111 to allow fluids to vent from the eye through the cannula 101 (e.g., see FIG. 7). In some embodiments, the vent 601 may hold the seal 111 in the open configuration to allow fluid (e.g., a gas or liquid) to vent through the cannula 101 to the exterior or the eye. For example, a gas (or another fluid) may flow through the cannula 101 and out of vent 601 during a procedure so that the exiting gas may be replaced with another fluid. The vent 601 may further include a rim 609 to provide a stop to limit an amount by which the vent 601 may be inserted into the seal 111. In some instances, a diameter of the rim 609 may be larger than an inner diameter of the trocar cannula 101.

The vent cannula 603 includes a tube portion 607 and a reduced portion 608. The rim 609 is disposed between the tube portion 607 and the reduced portion 608. In some implementations, the tube portion 607, the rim 609, and the reduced portion 608 may be formed form a single unitary piece. In other implementations, the tube portion 607, the rim 609, and the reduced portion 608 may be separate components. The tube portion 607 has a larger outer diameter than the reduced portion 608. Further, the reduced portion 608 may have an outer diameter that is smaller than an inner diameter of trocar cannula 101 to allow the vent cannula 603 to slide past the seal 111 and into the trocar cannula 101. The vent cannula 603 may be formed from a metal, such as, stainless steel or titanium, or other applicable material.

In some embodiments, the vent 601 may be a separate device from the valved trocar cannula 110 to allow the vent 601 to be inserted and removed without adding or removing parts of the valved trocar cannula 110 (e.g., without having to remove the overcap 103 from the cannula 101). The size of the vent 601 may also allow a user to handle the vent 601 with fingers or, for example, forceps, during the insertion and removal of the vent 601.

In some embodiments, the vent 601 may include a flexible tube 605 that frictionally engages an outer perimeter of the tube portion 607 of the vent cannula 603. In some instances, the flexible tube 605 may be formed from silicone or other polymeric material. The tube 605 may provide a visual indicator (e.g., be at least partially transparent) of the venting process. That is, where the tube 605 is formed at least partially of a transparent material, a substance overflowing from the eye may flow into the tube 605 and be readily apparent and visible to a user. In some embodiments, the tube 605 may be used as a grasping surface to remove the vent 601 from the cannula 101 (e.g., to assist grasping by fingers or forceps). FIG. 6b illustrates several example dimensions (provided in inches), according to an example embodiment. These dimensions are provided merely as example. Consequently, other dimensions are also contemplated. In some embodiments, the dimensions of the vent 601 may allow for the passage of instruments through the vent 601 when the vent 601 is positioned so as to extend through the seal 111.

Figure 8:
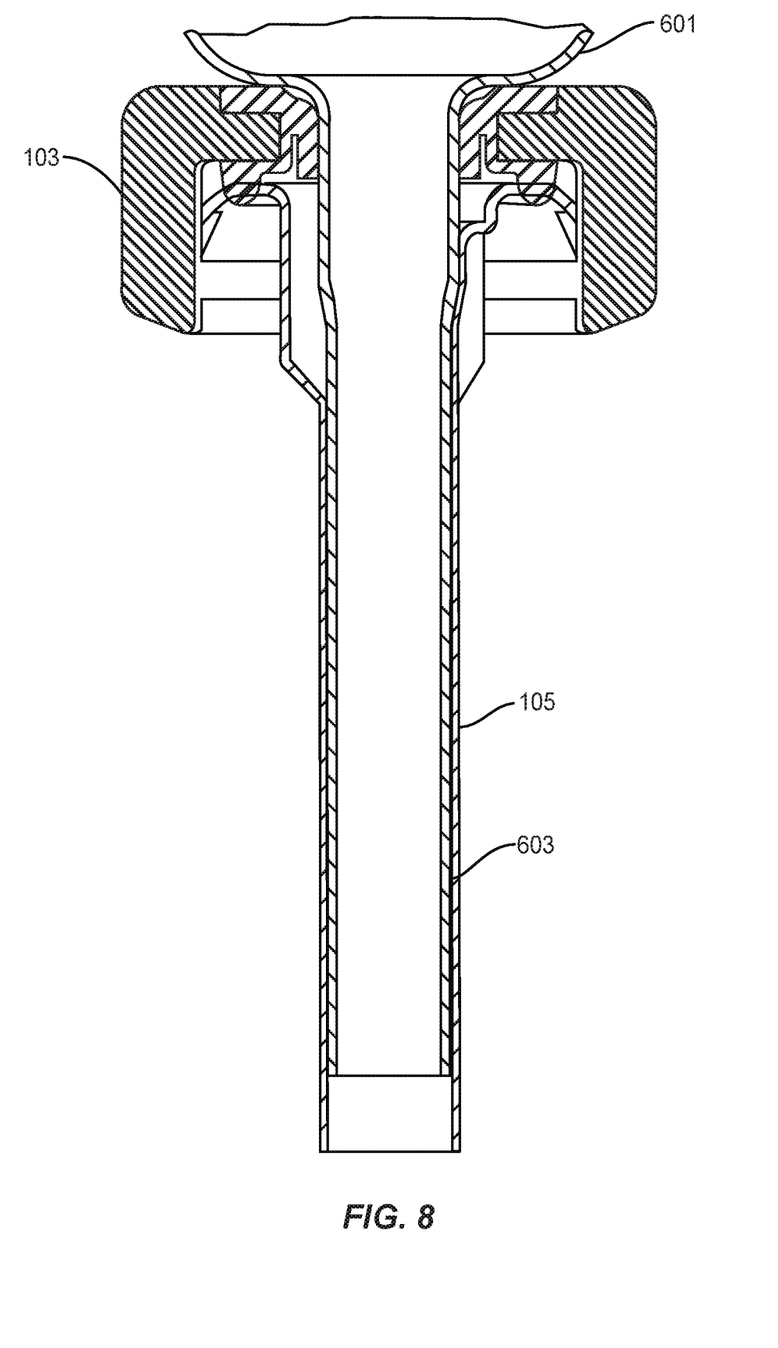
FIG. 8 is a cross-sectional view of an example valved trocar cannula.

FIG. 8 illustrates a cross section of the valved trocar cannula 110 with the vent 601 inserted therein.

Referring back to FIGS. 4b and 4c, it can be seen that the slit 113 in the seal 111 is generally perpendicular to the surfaces 112 and 114 of the seal 111. Typically, such a slit 113 may be a single slit, tri-slit, or cross-shaped slit. One problem with perpendicular slits, however, is that they may tend to open as the intraocular pressure increases, creating more leakage and even allowing streams of fluid to be ejected from the eye, through the cannula. This leakage may particularly occur when instruments are removed from valved trocar cannula. Leakage creates increased turbulence and fluid swirling in the eye adjacent to delicate retina tissue. Once outside the eye, fluid can stream onto microscope optics, the surgeon, staff, or floor creating annoyance and potential safety/contamination issues.

The leakage problem exists because apposition of the edges of perpendicular slits can be poor. When instruments are passed through the slit and then removed again, the sides of the slits must elastically return to their initial positions in order to form a good seal and to prevent leakage through the slit. The sides of the slit may fail to return to their initial positions, however, because of intraocular pressure and/or because of distortion of their originally planar shapes, e.g., due to sterilization or mechanical stretching and distortion due to manipulation of instruments inserted into the valved trocar cannula being during surgery.

Figure 9A:
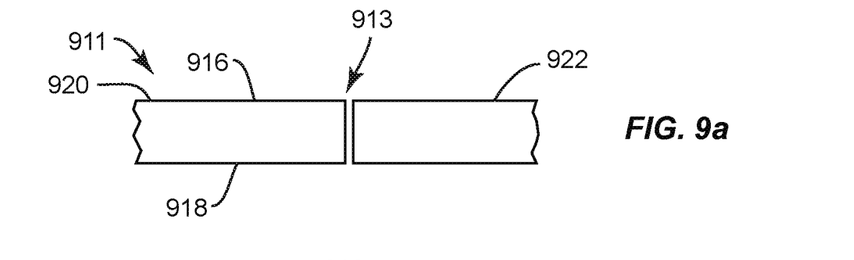
FIGS. 9a and 9b illustrate cross-sectional views of a perpendicular slit formed in a cannula seal.

FIG. 9a illustrates a cross-sectional view of an example elastomeric membrane 911, which may include, for example, all or part of a seal 111 as described above. In this example, slit 913 is perpendicular to the first surface 916 and second surface 918 of the elastomeric membrane. In FIG. 9a, the opposing sides 920, 922 of slit 913 are aligned well, e.g., as they might appear before instruments are passed through the slit 913.

Figure 9B:
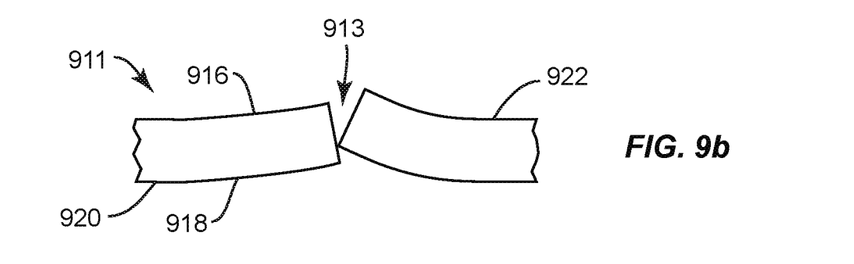

FIG. 9b shows a cross-sectional view of the same elastomeric membrane 911 after insertion and subsequent removal of a device, such as a surgical instrument, through the slit 913 and while intraocular pressure is applied to the second surface 918. In this situation, the opposing sides 920, 922 of slit 913 have failed to return to proper alignment with each other. It will be appreciated that this lack of alignment, along the length of the slit 913, increases the risk for leakage.

Figure 10A:
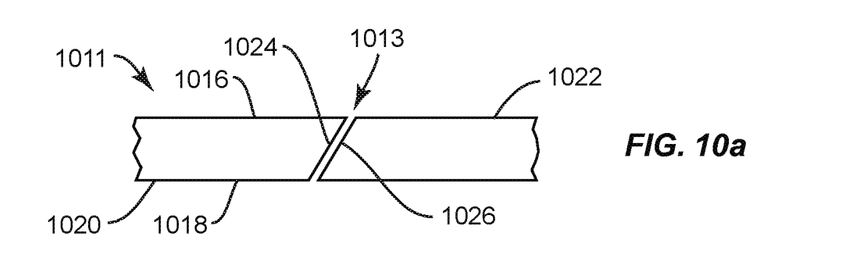
FIGS. 10a and 10b illustrate cross-sectional views of a non-perpendicular slit formed in a cannula seal.
Figure 10B:
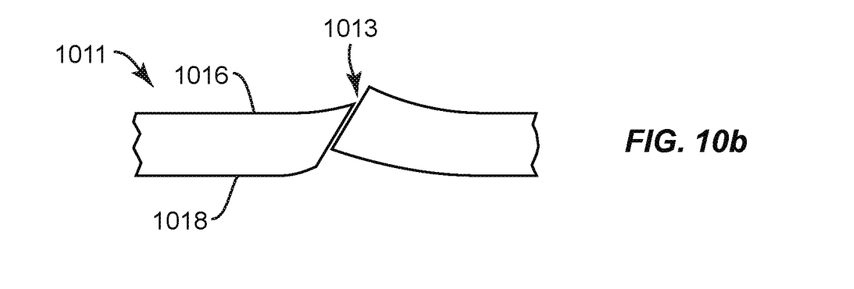

FIG. 10a illustrates an example elastomeric membrane 1011 according to some embodiments of the present disclosure. In the illustrated example, the slit 1013, extends through the elastomeric membrane at an oblique angle relative to the first surface 1016 and second surface 1018 along at least a portion of a length of the slit 1013, e.g., along an entirety or a majority of a length of the slit 1013. Consequently, in the example shown in FIGS. 10a and 10b, the slit is not perpendicular to the first and second surfaces 1016 and 1018. In this example, the slit 1013 forms approximately a 60-degree angle with respect to the first surface 1016 and second surface 1018. Here, the geometry of the slit is designed to use intraocular pressure to create apposition of one elastomeric edge against the other like a flap. As a result, the edges 1024 and 1026 of sides 1020 and 1022, respectively, forms an overlapping "valve seat" that prevents leakage at increasingly higher pressures, even after insertion and removal of an instrument through the slit 1013, as shown in FIG. 10b. Consequently, the design of slit 1013 reduces the risk of leakage, particularly as compared to the design of slit 913.

Figure 11:
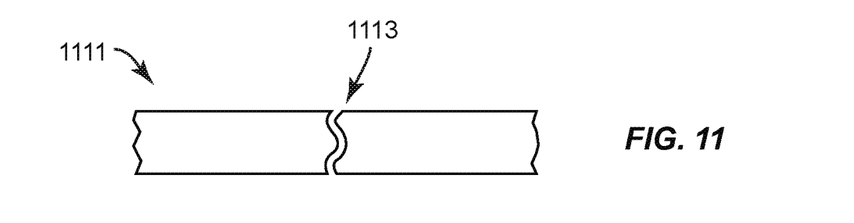
FIG. 11 illustrates another example of a non-perpendicular slit formed in a cannula seal.

This non-perpendicular slit geometry of slit 1013 encompasses the slit 1013 having an oblique angle (e.g., an angle that is not 90 degrees relative to the first or second surfaces 1020, 1022), and the slit 1013 may be formed by mechanical blades and tools. In some instances, non-perpendicular slit geometry may include a slit forming an angle between about 40 and 75 degrees, for example. In some embodiments, the slit geometry may be more complex, such as the example slit 1113 shown in FIG. 11. The slit 1113 may form a circuitous or serpentine shape and may be formed using a laser, such as a femtosecond laser, rather than a mechanical blade. Such a circuitous shape through the elastomeric membrane is believed to improve leakage prevention, while simultaneously avoiding undue mechanical or frictional forces on an instrument as it inserted through or removed from the slit. In some instances, a slope of a slit having a serpentine shape varies along all or a portion of the slit. In some instances, the slope along a portion of the slit having a serpentine shape forms an oblique angle relative to the first surface and/or second surface of the elastomeric membrane. As shown in FIG. 11, the slit 1113 is formed in an elastomeric membrane 1111.

Slit geometries as described above may be incorporated into an elastomeric membrane used to provide a seal in a closed cannula system like the system shown in FIGS. 1-8 where such slits are provided to allow insertion and removal of surgical tools into and through a cannula positioned in an eye during a surgical procedure. Such slit geometries may also be incorporated into elastomeric membranes used in any of a variety of other closed cannulas as well. In view of the discussion above, it will be appreciated that some embodiments of ophthalmic surgical apparatus incorporating the inventive techniques described herein include a cannula configured for insertion into an eye, e.g., as shown in FIG. 12, where the valved trocar cannula 110 is inserted into the eye 1401, through a wound or incision formed in the sclera 1403 and into the vitreous body 1405, and arranged so that a distal end 1402 of the valved trocar cannula 110 is positioned in the eye 1401 and a proximal end 1404 of the valved trocar cannula 110 is positioned outside the eye 1401. In these embodiments, an elastomeric membrane, e.g., as shown in FIGS. 10-11, is disposed at the proximal end 1404 of the valved trocar cannula 110 and attached thereto so as to restrict a free flow of fluid, e.g., liquid, from within the valved trocar cannula 110 to outside the proximal end 1404 of the valved trocar cannula 110. The elastomeric membrane includes at least one slit, e.g., slit 113, 913, 1013, or 1113, extending through the elastomeric membrane and arranged to permit the passage of a surgical tool or other device into the valved trocar cannula 110 therethrough. This slit has a length L and extends along both the first and second surfaces of the elastomeric membrane. As discussed in detail above, in some instances, the slit extends through the elastomeric membrane at an oblique angle (as measured relative to the first and second surfaces of the elastomeric membrane) along an entirety or a majority of the length of the slit. With this arrangement, pressure applied across the first or second surfaces of the elastomeric membrane in the vicinity of the slit tends to keep the slit in a closed position.

In some embodiments, as discussed above, the slit extends through the elastomeric membrane at an angle of less than about 75 degrees, relative to the first and second surfaces of the elastomeric membrane. In some embodiments, the slit extends through the elastomeric membrane at an angle of about 45 degrees, relative to the first and second surfaces of the elastomeric membrane. In some embodiments, the slit changes direction continuously or at one or more points as it extends through the elastomeric membrane.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A valved trocar cannula comprising:
   a cannula sized and shaped to be inserted into a body, the cannula comprising a distal end configured to be positioned within the body when in use and a proximal end configured to be positioned outside the body when in use; and
   an elastomeric membrane comprising:
   a first surface at a proximal end of the elastomeric membrane;
   a second surface at a distal end of the elastomeric membrane;
   a thickness extending from the first surface to the second surface; and
   at least one slit, having a serpentine shape along the thickness of the elastomeric membrane, extending through the thickness of the elastomeric membrane and at least a portion of the slit forming an oblique angle, relative to the first surface and second surface, through the thickness of the elastomeric membrane, the slit having a length extending along at least a portion of the first surface and along at least a portion of the second surface of the elastomeric membrane and arranged to permit the passage of a surgical instrument through the elastomeric membrane and into the cannula, the elastomeric membrane disposed at the proximal end of the cannula and connected to the cannula and restricting a free flow of fluid from within the cannula to outside the proximal end of the cannula;
   wherein the slit changes direction at least twice through the thickness of the elastomeric membrane and wherein both sides of the slit form complementary profiles to each other along the thickness of the elastomeric membrane.

2. The valved trocar cannula of claim 1, wherein the oblique angle formed by the slit extends through the elastomeric membrane along a majority of the length of the slit.

3. The valved trocar cannula of claim 1, wherein at least a portion of the oblique angle is less than approximately 75 degrees.

4. The valved trocar cannula of claim 1, wherein at least a portion of the oblique angle is approximately 45 degrees.

5. The valved trocar cannula of claim 1 further comprising:
   an overcap coupled to the proximal end of the cannula, the elastomeric membrane attached to a proximal end of the overcap.

6. The valved trocar cannula of claim 1, wherein the slit is a laser cut slit.

7. The valved trocar cannula of claim 1, wherein the slit is straight along the length of the slit extending along the first surface.

8. The valved trocar cannula of claim 5, wherein the overcap comprises a plurality of apertures formed in the proximal end thereof, the elastomeric membrane received into the plurality of apertures.

9. The valved trocar cannula of claim 5, wherein the overcap comprises at least one slot formed in a side of the overcap, and wherein the cannula comprises at least one tab, the at least one tab received into the at least one slot to form an interlocking connection between the overcap and the cannula.

10. The valved trocar cannula of claim 5, wherein the overcap defines a flange defining an opening, and wherein the elastomeric membrane sandwiches the flange between a first end and a second end of the elastomeric membrane.

11. The valved trocar cannula of claim 9, wherein the interlocking connection between the overcap and the cannula prevent rotation of the overcap relative to the cannula.

* * * * *